United States Patent
Gatrell et al.

(10) Patent No.: US 11,446,041 B2
(45) Date of Patent: Sep. 20, 2022

(54) KNEE CHAMFER BLOCK GUIDE WITH 3D PRINTED UNDERCUT SAW SLOT

(71) Applicant: ETHICON LLC, Guaynabo, PR (US)

(72) Inventors: Bernice A. Gatrell, Columbia City, IN (US); Rakshak Nemiraj, Warsaw, IN (US); Alexander D. Jones, Warsaw, IN (US)

(73) Assignee: Cilag GmbH International, Zug (CH)

( * ) Notice: Subject to any disclaimer, the term of this patent is extended or adjusted under 35 U.S.C. 154(b) by 146 days.

(21) Appl. No.: 16/182,825

(22) Filed: Nov. 7, 2018

(65) Prior Publication Data

US 2020/0138452 A1    May 7, 2020

(51) Int. Cl.
*A61B 17/15*    (2006.01)
*A61B 17/16*    (2006.01)
*A61B 17/17*    (2006.01)

(52) U.S. Cl.
CPC .......... *A61B 17/155* (2013.01); *A61B 17/157* (2013.01); *A61B 17/1675* (2013.01); *A61B 17/1764* (2013.01)

(58) Field of Classification Search
CPC .................................................... A61B 17/155
See application file for complete search history.

(56) References Cited

U.S. PATENT DOCUMENTS

| | | | | |
|---|---|---|---|---|
| 5,129,909 | A * | 7/1992 | Sutherland | A61B 17/155 606/53 |
| 10,111,673 | B2 * | 10/2018 | Edwards | A61B 17/155 |
| 2013/0310836 | A1 * | 11/2013 | Raub | A61B 17/155 606/84 |
| 2017/0027587 | A1 * | 2/2017 | Fraone | A61B 17/155 |
| 2018/0185097 | A1 * | 7/2018 | Langhorn | A61B 34/10 |

FOREIGN PATENT DOCUMENTS

| | | |
|---|---|---|
| AU | 2016 231 338 A1 | 10/2017 |
| WO | WO 94/14366 A2 | 7/1994 |
| WO | WO 2015/112566 A1 | 7/2015 |

OTHER PUBLICATIONS

European Search Report and Written Opinion dated Mar. 31, 2020 for Application No. EP 19207667.7, 7 pgs.

* cited by examiner

*Primary Examiner* — Nicholas W Woodall
(74) *Attorney, Agent, or Firm* — Frost Brown Todd LLC (57) ABSTRACT

A bone saw cutting guide block includes a body and a bone saw guide assembly. The body includes a proximal surface and a distal surface. The bone saw guide assembly includes a first guide slot defined by the body. The first guide slot extends through the proximal surface and the distal surface along an insertion and retraction path. The first guide slot may accommodate lateral movement of a bone saw while guiding the bone saw along the insertion and retraction path. The first guide slot includes a first interior surface and a second interior surface. The first interior surface is spaced a first distance transversely away from the insertion and retraction path. The second interior surface is spaced a second distance transversely away from the insertion and retraction path. The first distance is smaller than the second distance.

19 Claims, 10 Drawing Sheets

KNEE CHAMFER BLOCK GUIDE WITH 3D PRINTED UNDERCUT SAW SLOT

BACKGROUND

In some instances, a block guide defining slots may be used to guide a bone saw in removing various portions of bone. One example includes the use of a knee chamfer block guide during a knee replacement. A knee replacement, also called arthroplasty, is a surgical procedure to resurface a knee damaged by arthritis or a severe knee injury. Metal and/or plastic prostheses are used to cap the ends of the resurfaced femur and tibia that form the knee joint, along with the knee cap. In order to resurface the femoral portion of the knee, a plurality of cuts may be made on the femur. After a first cut is made on the end of the femur, a suitably sized knee chamfer block guide may be attached to the newly exposed surface of the femur. A bone saw may be inserted through guide slots defined by the knee chamfer block guide to provide precise cuts in order to suitably resurface the femur for attaching a corresponding femoral prosthesis.

Three-dimensional (3D) printing is an additive printing process used to make three-dimensional solid objects from a digital model. 3D printing may be used in rapid product prototyping, product manufacturing, mold generation, and mold master generation. 3D printing techniques are considered additive processes because they involve the application of successive layers of material. This is unlike traditional machining processes, which often rely upon the removal of material to create the final object. Various materials may be used in 3D printing. For example, materials such as polymide, alumide, titanium, or thermoplastic polyurethane may be used in 3D printing. Some 3D printing techniques utilize powder as the basic material, then transform the powder into a desired shape to form a product. For example, laser sintering involves applying successive thin layers of powder, one layer on top of the next. Between application of each layer of powder, a laser travels over desired portions of the current powder layer and sinters targeted powder together, eventually forming the desired shape. Once complete, the final product may be removed from the unsintered powder.

While various kinds of bone cutting guide blocks have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Cutting Guide Block

Figure 1A:
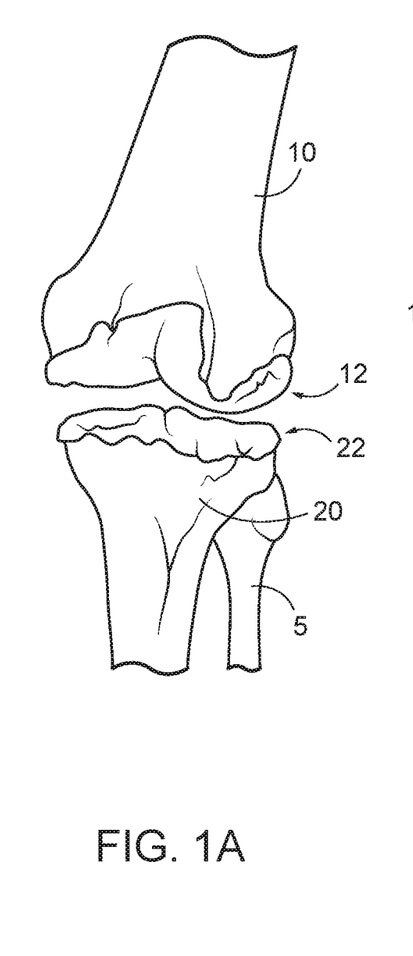
FIG. 1A depicts a perspective view of bones of a knee having end-stage knee arthritis.
Figure 1B:
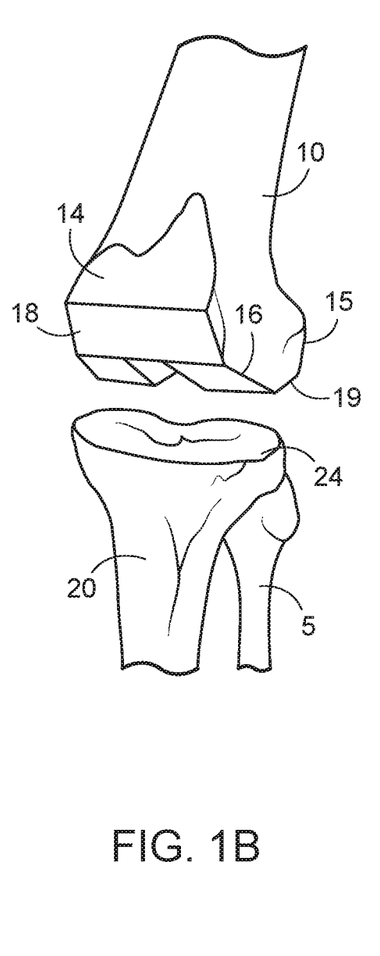
FIG. 1B depicts a perspective view of the bones of FIG. 1A after having been resurfaced in preparation of having a knee prosthesis attached.
Figure 1C:
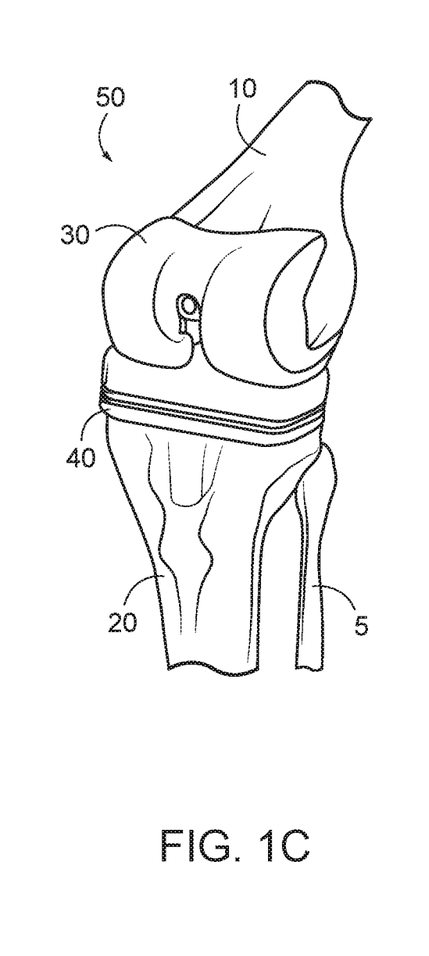
FIG. 1C depicts a perspective view of a knee prosthesis attached to the resurfaced bones of FIG. 1B.

A knee having arthritis (12, 22), similar to that shown in FIG. 1A, or other severe damage may be a good candidate for a knee replacement surgery. In a knee replacement surgery, a femur (10) and tibia (20) having respective arthritic portions (12, 22) (as shown in FIG. 1A), are resurfaced (as shown in FIG. 1B) to remove the damaged portions of the knee, and then capped with respective prosthesis components (30, 40) (as shown in FIG. 1C). A resurfaced tibia (20) may only require a superior transverse cut (24) to accommodate tibial prosthesis component (40). However, a resurfaced femur (10) may require a plurality of cuts in order to accommodate femoral prosthesis component (30). In some instances, a resurfaced femur (10) may require an anterior coronal cut (14), a posterior coronal cut (15), a transverse cut (16), an anterior chamfer cut (18), and a posterior chamfer cut (19) in order to suitably resurface femur (10) to accommodate femoral prosthesis component (30).

A four-in-one cutting guide block (60) may be used in order to guide a reciprocating bone saw (90) in making four cuts, such that the four cuts are made precisely relative to each other. In particular, as will be described in greater detail below, four-in-one cutting guide block (60) may assist in making the coronal cuts (14, 15) as well as the chamfer cuts (18, 19).

Figure 2:
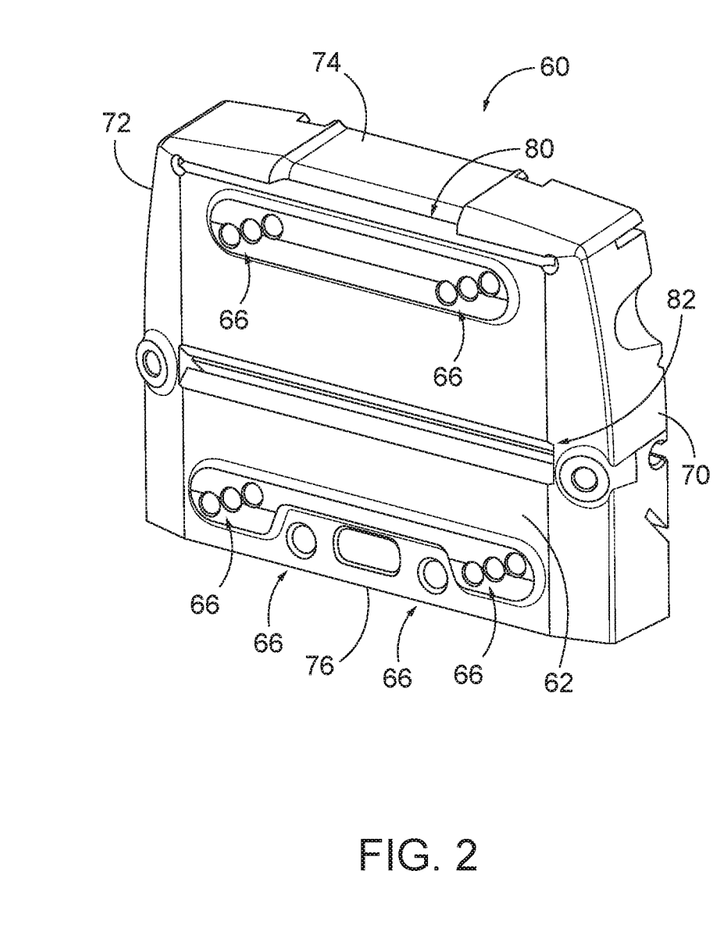
FIG. 2 depicts a perspective view of an exemplary cutting guide block that may be used to resurface a femur in preparation of having a knee prosthesis attached.
Figure 3:
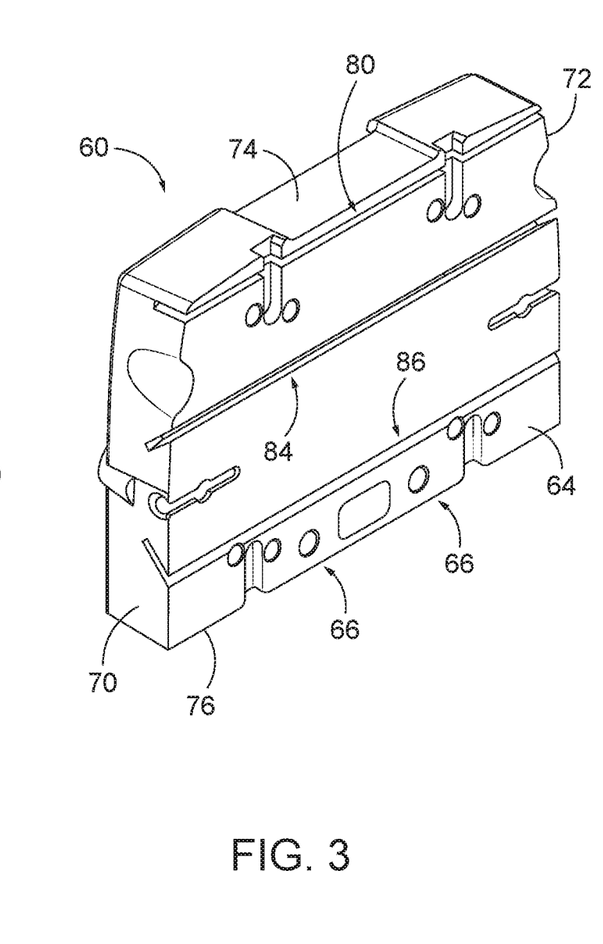
FIG. 3 depicts another perspective view of the cutting guide block of FIG. 2.

Cutting guide block (60) includes a proximal surface (62), a distal surface (64), a first lateral edge (70), a second lateral edge (72), a top edge (74), and a bottom edge (76). A plurality of through holes (66) extend from proximal surface (62) to distal surface (64). Through holes (66) are dimensioned to receive fastening components such that cutting guide block (60) may selectively attach to the femur (10) during resurfacing. Additionally, a portion of distal surface (64) is configured to abut against transverse cut (16) when cutting guide block (60) is attached to femur (10).

As mentioned above, cutting guide block (60) is configured to guide reciprocating bone saw (90) in making four cuts (14, 15, 18, 19). Therefore, as will be described in greater detail below, cutting guide block (60) defines a pair of coronal cut guide slots (80) and a pair of chamfer cut guide slots (84, 86).

Coronal cut guide slots (80) extend from proximal surface (62) to distal surface (64) and extend within the confines of lateral edges (70, 72). As best seen in FIGS. 4C-4F, one coronal cut guide slot (80) is located near top edge (74) to guide a reciprocating bone saw (90) to perform anterior coronal cut (14); while another coronal guide slot (80) is located near bottom edge (76) to guide reciprocating bone saw (90) to perform posterior coronal cut (15).

A chamfer cut entry slot (82) is defined by proximal surface (62). Chamfer cut entry slot (82) diverges into a first chamfer cut guide slot (84) and a second chamfer cut guide slot (86), each extending into distal surface (64). Chamfer cut entry slot (82) is dimensioned to receive reciprocating bone saw (90) such that bone saw (90) may also further extend into either chamfer cut guide slot (84, 86). First chamfer cut guide slot (84) is located to guide reciprocating bone saw (90) to perform anterior chamfer cut (18); while second chamfer cut guide slot (86) is located to guide reciprocating bone saw (90) to perform posterior chamfer cut (19).

Guide slots (80, 84, 86) and entry slot (82) are located between lateral edges (70, 72) so that guide block (60) may remain in one individual piece. In other words, if guide slots (80, 84, 86) and entry slot (82) extend from lateral edge (70) all the way through lateral edge (72), guide block (60) would be divided into multiple pieces, which may reduce the precision of the four bone cuts (14, 15, 18, 19) relative to each other.

Figure 4A:
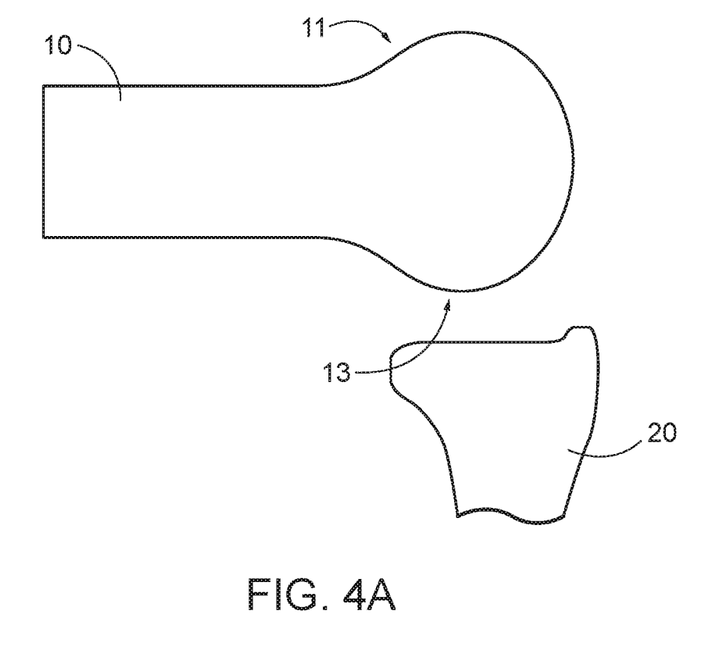
FIG. 4A depicts a cross-sectional view, taken along a sagittal plane, of a femur and tibia in an angularly offset configuration.

FIGS. 4A-4H show an exemplary process of resurfacing and capping of the femoral portion (10) of the knee. FIG. 4A shows the femur (10) of a patient and tibia (20) in an angularly offset relationship, for reference. With tibia (20) in the angularly offset position, an anterior portion (11) of femur (10) faces away from tibia (20), while a posterior portion (13) of femur (10) faces toward tibia (20).

Figure 4B:
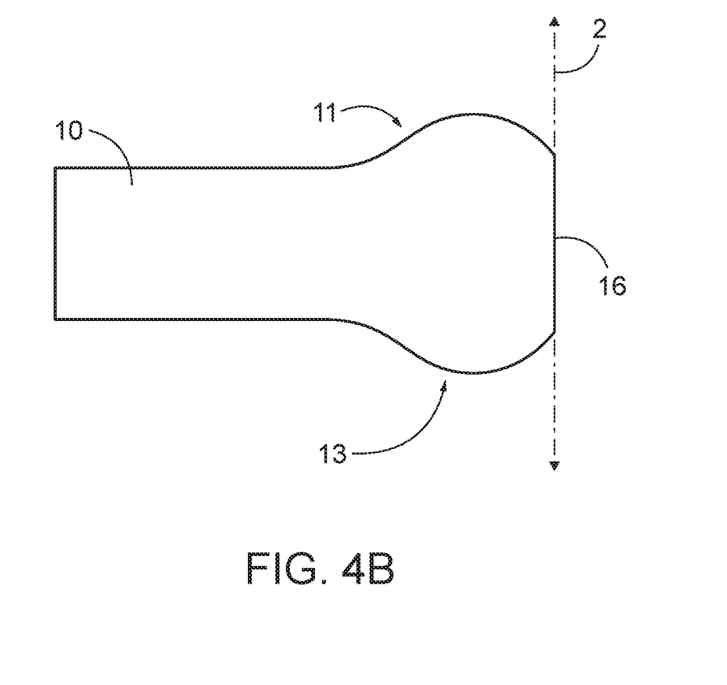
FIG. 4B depicts a cross-sectional view, taken along a sagittal plane, of the femur of FIG. 4A, with a transverse cut on an end of the femur.

An operator may first make transverse cut (16) on femur (10) by inserting reciprocating bone saw (90) along an insertion and retraction path (2). Any suitable guiding mechanism may be used to guide bone saw (90) along path (2) to make cut (16) on femur (10) as would be apparent to one having ordinary skill in the art in view of the teachings herein. It should be understood that reciprocating bone saw (90) reciprocates back and forth in a sawing motion that is into and out of the page, and thus transverse to the insertion and retraction path (2), to make cut (16) while being inserted against femur (10) along path (2). Therefore, as bone saw (90) is inserted along path (2) to make transverse cut (16) on femur (10), the motion back and forth into and out of the page is what makes the sawing motion to cut bone, and not the motion along path (2).

Figure 4C:
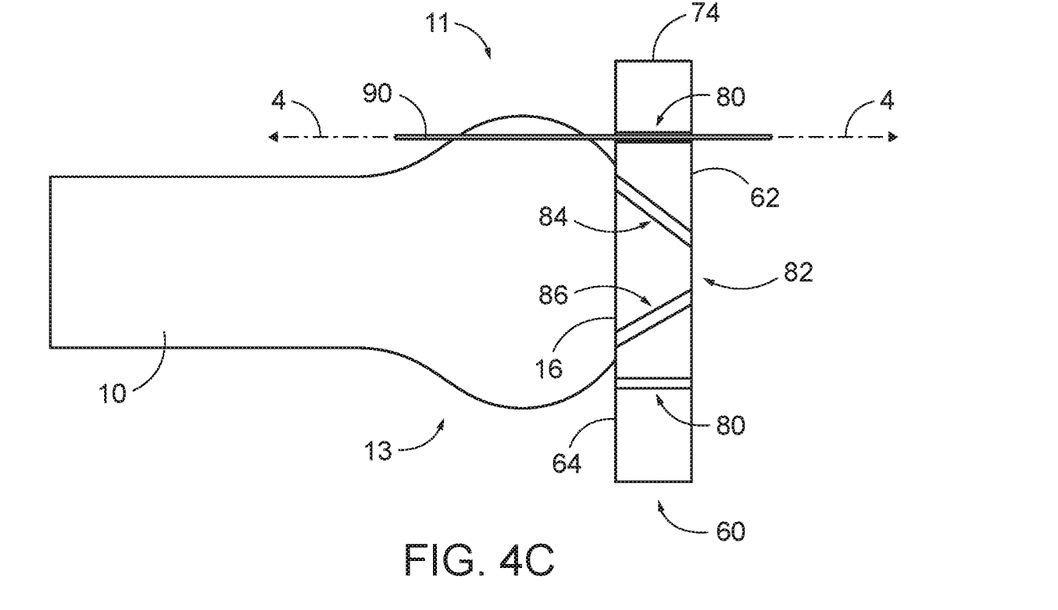
FIG. 4C depicts a cross-sectional view, taken along a sagittal plane, of the femur of FIG. 4A, where the cutting guide block of FIG. 2 is attached to the first cut of FIG. 4B, where a bone saw is inserted through a coronal cut guide slot of the cutting guide block to make an anterior coronal cut on the femur.

Next, as shown in FIG. 4C, cutting guide block (60) may be attached to femur (10) utilizing any means that would be apparent to one having ordinary skill in the art in view of the teachings herein. For example, fastening elements such as pins, screws, etc., may be temporarily inserted into through holes (66) and into the portion of femur (10) exposed by cut (16) in order to suitably attach cutting guide block (60) to femur (10). Such fastening elements may be removed after the cutting process is complete. Cutting guide block (60) may come in different sizes for different sized prostheses (30). The operator may use any suitable method to determine what size cutting guide block (60) should be used as would be apparent to one having ordinary skill in the art in view of the teachings herein.

Figure 4D:
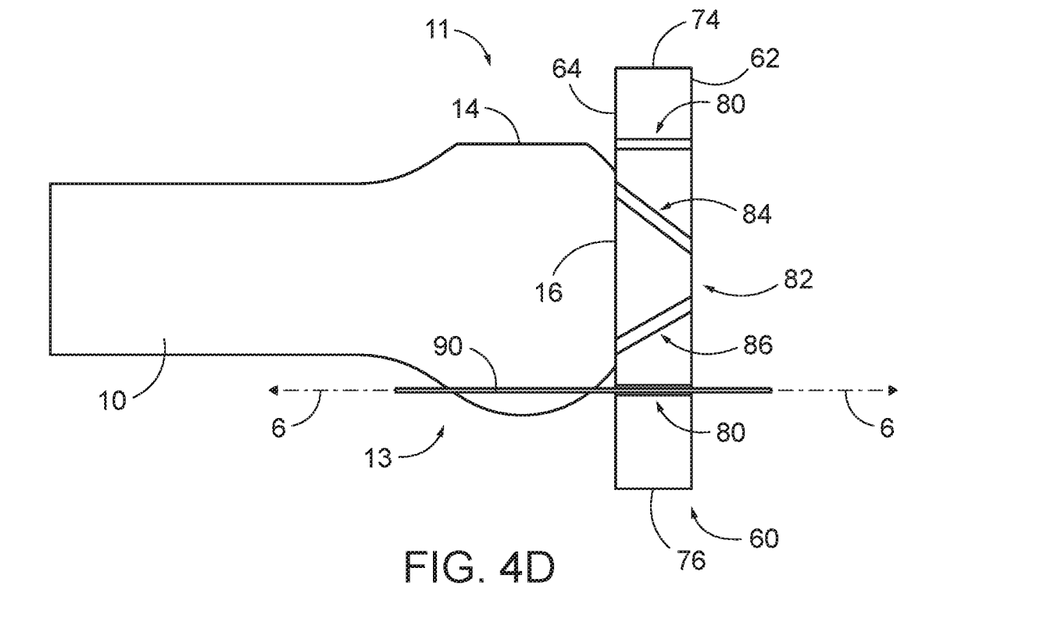
FIG. 4D depicts a cross-sectional view, taken along a sagittal plane, of the femur of FIG. 4A, where the cutting guide block of FIG. 2 is attached to the first cut of FIG. 4B, where a bone saw is inserted through another coronal cut guide slot of the cutting guide block to make a posterior coronal cut on the femur.

With the appropriately sized cutting guide block (60) suitably attached to femur (10), the operator may then insert reciprocating bone saw (90) into various guide slots (80, 84, 86) in order to make appropriately sized cuts (14, 15, 18, 19) relative to each other. Therefore, as also shown in FIG. 4C, the operator may make anterior coronal cut (14) by inserting reciprocating bone saw (90) along insertion and retraction path (4) such that bone saw (90) enters coronal cut guide slot (80) near top edge (74) via proximal surface (62) and extends past distal surface (64) to complete anterior coronal cut (14). Next, as shown in FIG. 4D, the operator may make posterior coronal cut (15) by inserting reciprocating bone saw (90) along insertion and retraction path (6) such that bone saw (90) enters coronal cut guide slot (80) near bottom edge (76) via proximal surface (62) and extends past distal surface (64) to complete posterior coronal cut (15).

It should be understood that reciprocating bone saw (90) reciprocates back and forth in a sawing motion that is into and out of the page to make cuts (14, 15) while being inserted against femur (10) along insertion and retraction paths (4, 6), such that the reciprocation is along a path transverse to the respective path (4, 6). Therefore, as bone saw (90) is inserted along paths (4,6) to make coronal cuts (14, 15) on femur (10), the motion back and forth into and out of the page is what makes the sawing motion to cut bone, and not the motion along paths (4, 6).

Figure 4E:
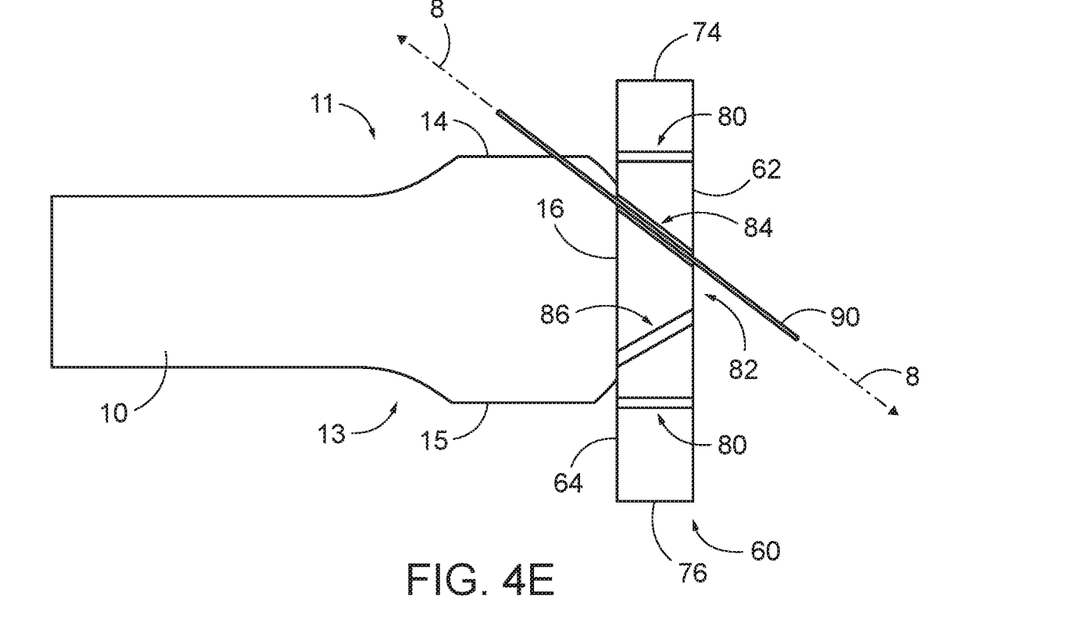
FIG. 4E depicts a cross-sectional view, taken along a sagittal plane, of the femur of FIG. 4A, where the cutting guide block of FIG. 2 is attached to the first cut of FIG. 4B, where a bone saw is inserted through a chamfer cut guide slot of the cutting guide block to make an anterior chamfer cut on the femur.
Figure 4F:
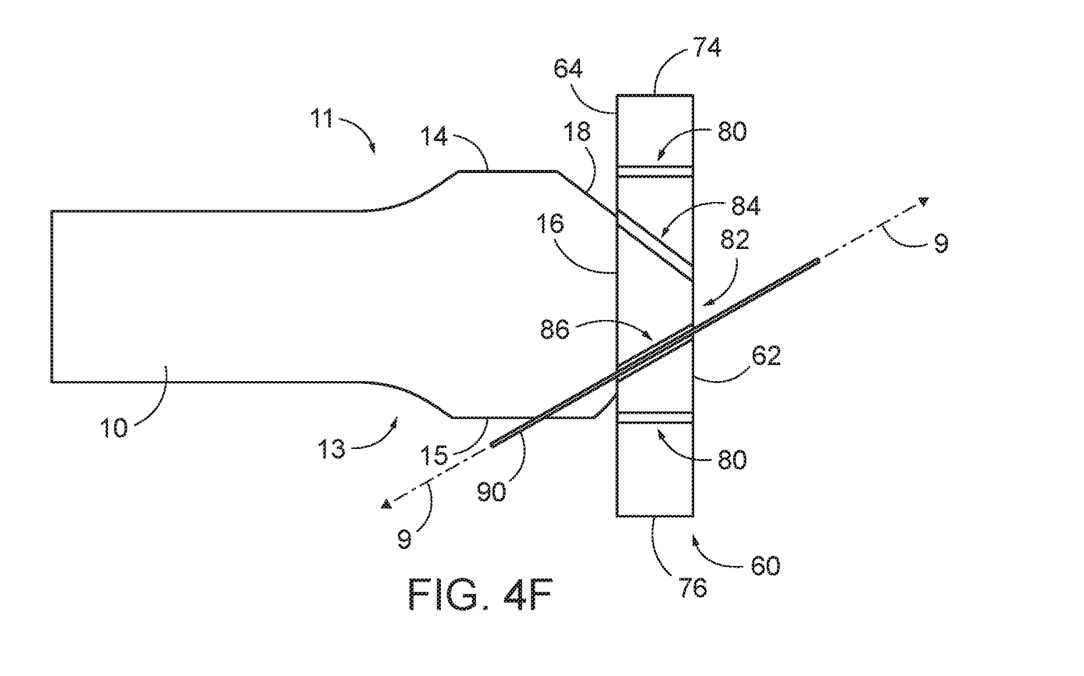
FIG. 4F depicts a cross-sectional view, taken along a sagittal plane, of the femur of FIG. 4A, where the cutting guide block of FIG. 2 is attached to the first cut of FIG. 4B, where a bone saw is inserted through another chamfer cut guide slot of the cutting guide block to make a posterior chamfer cut on the femur.

Next, as shown in FIG. 4E, the operator may make anterior chamfer cut (18) by inserting reciprocating bone saw (90) along insertion and retraction path (8) such that bone saw (90) enters chamfer cut entry slot (82), extends into first chamfer cut guide slot (84), and extends past distal surface (64) to complete anterior chamfer cut (18). Next as shown in FIG. 4F, the operator may make posterior chamfer cut (19) by inserting reciprocating bone saw (90) along insertion and retraction path (9) such that bone saw (90) enters chamfer cut entry slot (82), extends into second chamfer cut guide slot (86), and extends past distal surface (64) to complete posterior chamfer cut (19).

It should be understood that reciprocating bone saw (90) reciprocates back and forth in a sawing motion that is into and out of the page to make cut (18, 19) while being inserted against femur (10) along insertion and retraction paths (8, 9), such that the reciprocation is along a path transverse to the respective path (8, 9). Therefore, as bone saw (90) is inserted along paths (8, 9) to make chamfer cuts (18, 19) on femur (10), the motion back and forth into and out of the page is what makes the sawing motion to cut bone, and not the motion along paths (8, 9). While the example shows cuts (14, 15, 18, 19) being made in a certain order, it should be understood any other suitable order of making cuts (14, 15, 18, 19) may be utilized as would be apparent to one having ordinary skill in the art in view of the teachings herein.

Figure 4G:
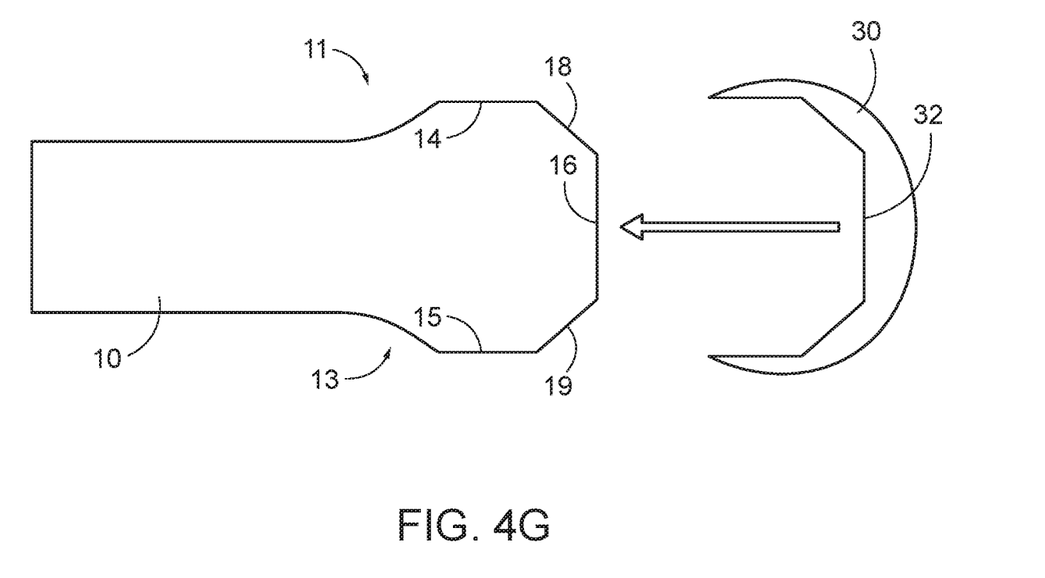
FIG. 4G depicts a cross-sectional view, taken along a sagittal plane, of the femur of FIG. 4A, where the femur is suitably resurfaced and a femoral prosthesis component is aligned with the femur.
Figure 4H:
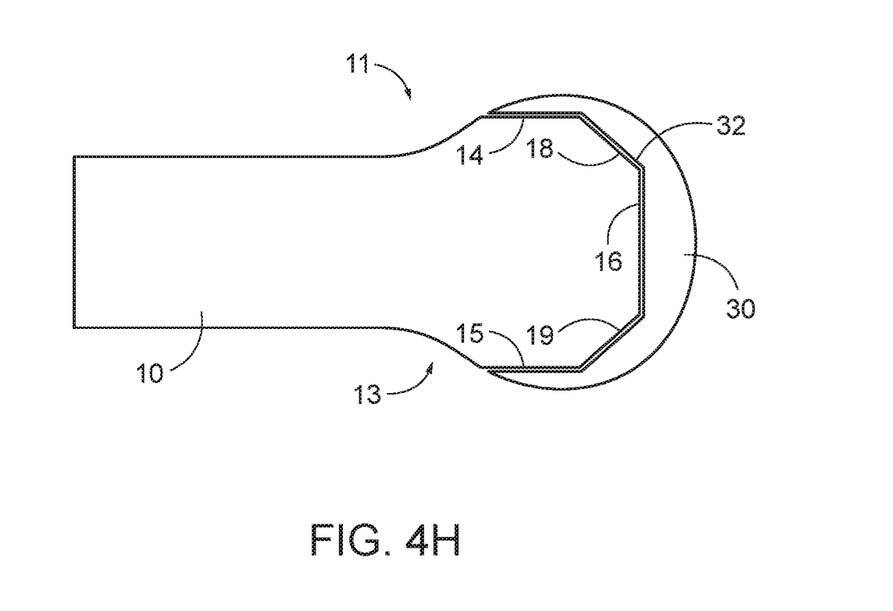
FIG. 4H depicts a cross-sectional view, taken along a sagittal plane, of the femur of FIG. 4A, where the femur is properly resurfaced and the femoral prosthesis component of FIG. 4G is suitably attached with the femur.

Next, with all cuts (14, 15, 16, 18, 19) having been made, the operator may suitably remove cutting guide block (60) by utilizing any means apparent to one having ordinary skill in the art in view of the teachings herein. With cutting guide block (60) removed, as shown in FIG. 4G, the operator may align a complementary interior surface (32) of femoral prosthesis component (30) with recently made cuts (14, 15, 16, 18, 19) and insert femoral prosthesis component (30) onto femur (10), as shown in FIG. 4H. The operator may couple femoral prosthesis component (30) on femur (10) using any suitable means as would be apparent to one having ordinary skill in the art in view of the teachings herein. For instance, bone cement may be used to couple femoral prosthesis component (30) with femur (10).

II. Alternative Exemplary Cutting Guide Block with 3D Printed Undercut Saw Slot In order to suitably guide reciprocating bone saw (90) to make precise bone cuts (14, 15, 18, 19), it may be desirable for saw guide slots (80, 84, 86) to be narrow enough to keep reciprocating bone saw (90) aligned with an insertion/retraction path during the sawing motion. Because bone saw (90) reciprocates back and forth into and out of the page when viewed from the perspective shown in FIGS. 4C-4F, bone saw (90) may contact the interior surfaces defining saw guide slots (80, 84, 86) during use of cutting guide block (60) with bone saw (90) to cut bone. Contact between bone saw (90) and the interior surfaces defining saw guide slots (80, 84, 86) while bone saw (90) reciprocates may cause large amounts of thermal energy to build up due to frictional contact. If too much heat builds up from such friction, undesirable consequences may occur, such as warping or weakening of bone saw (90), warping or other structural damage to interior surfaces defining saw guide slots (80, 84, 86), thermal damage to the bone, or other undesirable results. Therefore, it may be desirable to have a cutting guide block (60) with saw guide slots (80, 84, 86) that are still capable of suitably keeping bone saw (90) aligned with an insertion/retraction path; but also create less contact between bone saw (90) and the interior surfaces of guide slots (80, 84, 86) to thereby reduce friction and thereby prevent buildup up of excessive thermal energy.

Figure 5:
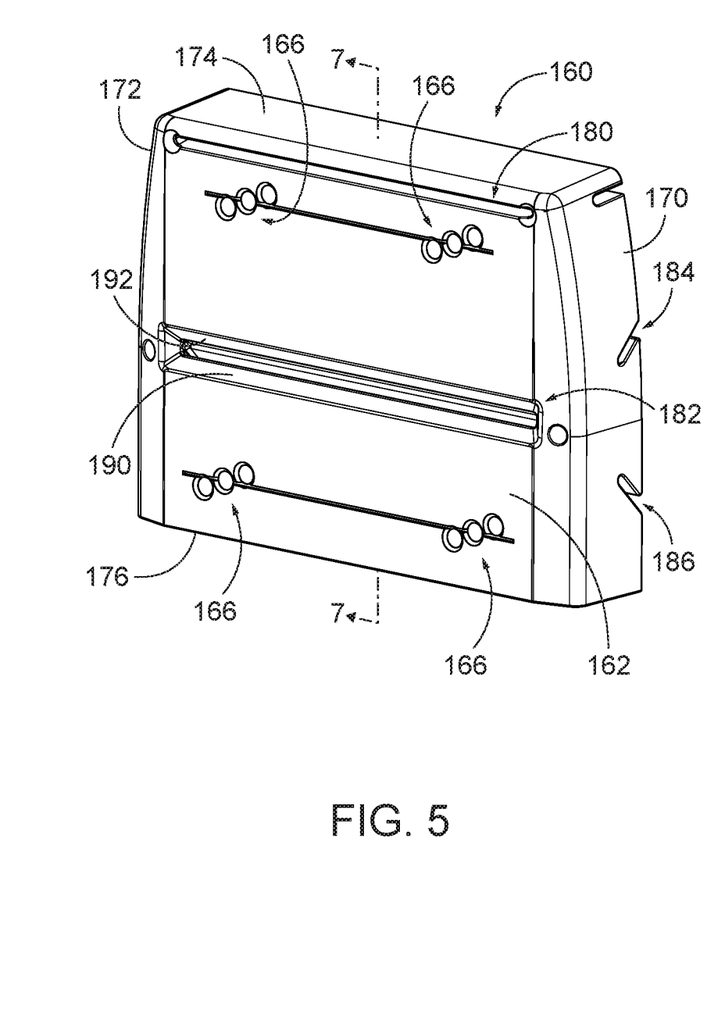
FIG. 5 depicts a perspective view of another exemplary cutting guide block that may be used to resurface a femur in preparation of having a knee prosthesis attached.
Figure 6:
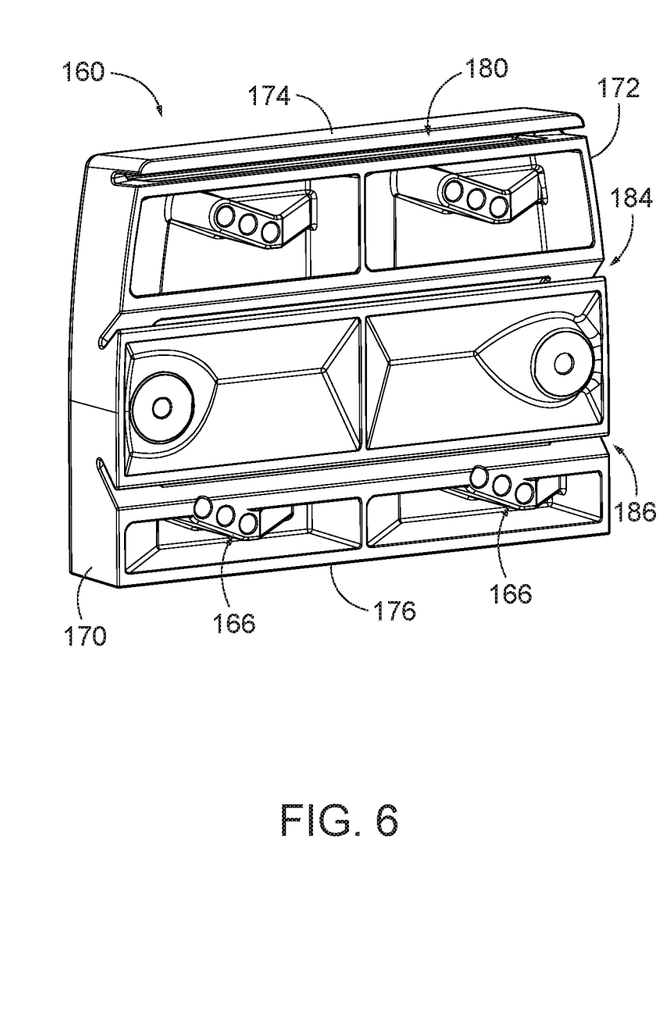
FIG. 6 depicts another perspective view of the cutting guide block of FIG. 5.
Figure 7:
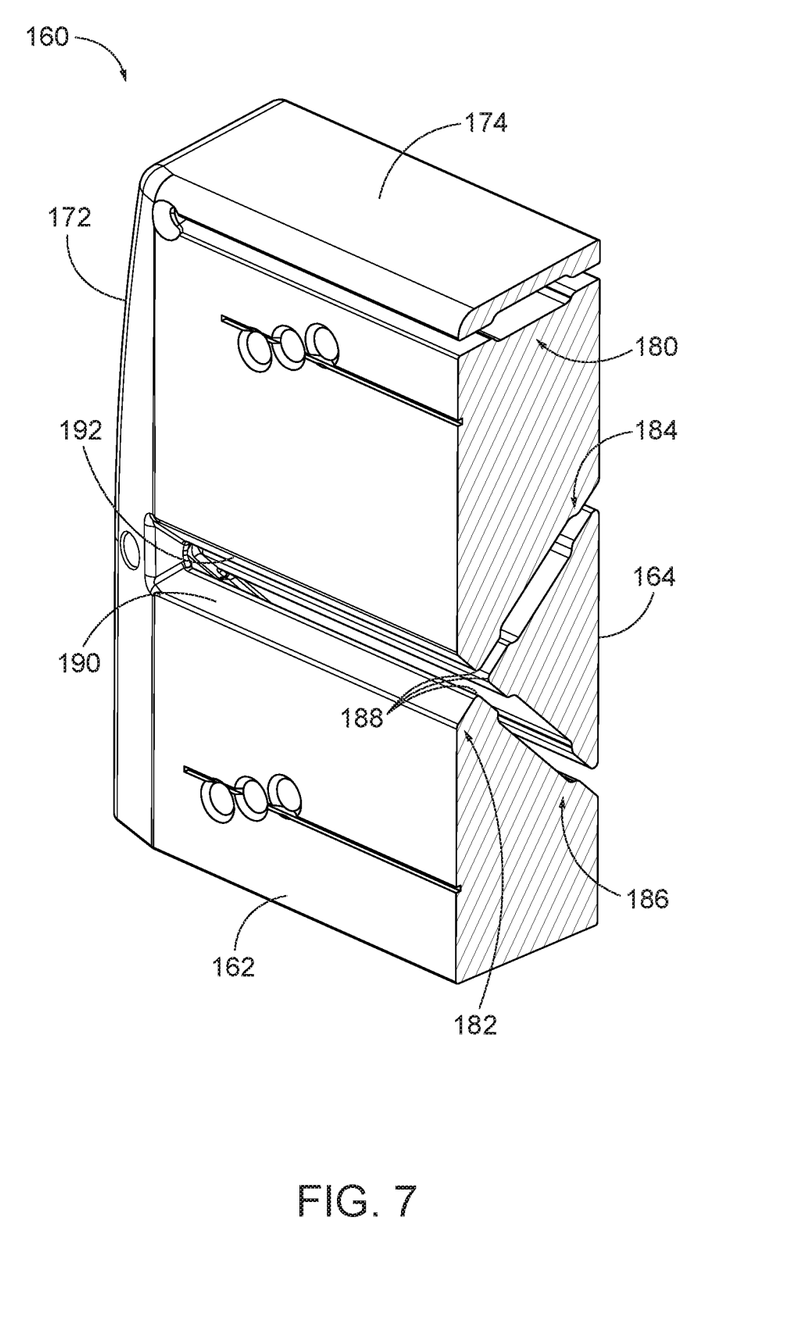
FIG. 7 depicts a cross-sectional perspective view of the cutting block of FIG. 5, taken along line 7-7 of FIG. 5.

FIGS. 5-7 show an exemplary 3D printed four-in-one cutting guide block (160) that may be used in order to guide a reciprocating bone saw (90) in making four cuts, such that the four cuts are made precisely relative to each other. Any suitable 3D printing process may be utilized to form four-in-one cutting guide block (160) as would be apparent to one having ordinary skill in the art in view of the teachings herein. Cutting guide block (160) is substantially similar to cutting guide block (60) described above, with differences elaborated below. Therefore, four-in-one cutting guide block (160) may assist in making the coronal cuts (14, 15) as well as the chamfer cuts (18, 19). However, cutting guide block (160) has guide slots (180, 184, 186) each having a recessed intermediate interior surface (114) dimensioned to define a gap with bone saw (90) while bone saw (90) reciprocates within guide slots (180, 184, 186) to saw bone.

Cutting guide block (160) includes a proximal surface (162), a distal surface (164), a first lateral edge (170), a second lateral edge (172), a top edge (174), and a bottom edge (176). A plurality of through holes (166) extend from proximal surface (162) to distal surface (164). Through holes (166) are dimensioned to receive fastening components (e.g., screws, pins, etc.) such that cutting guide block (160) may selectively attach to the femur (10) during resurfacing. Additionally, a portion of distal surface (164) is configured to abut against transverse cut (16) when cutting guide block (160) is attached to femur (10).

As mentioned above, cutting guide block (160) is configured to guide reciprocating bone saw (90) in making four cuts (14, 15, 18, 19). Therefore, similar to cutting guide block (60) described above, with difference elaborated below, cutting guide block (160) defines a pair of coronal cut guide slots (180) and a pair of chamfer cut guide slots (184, 186).

Figure 8:
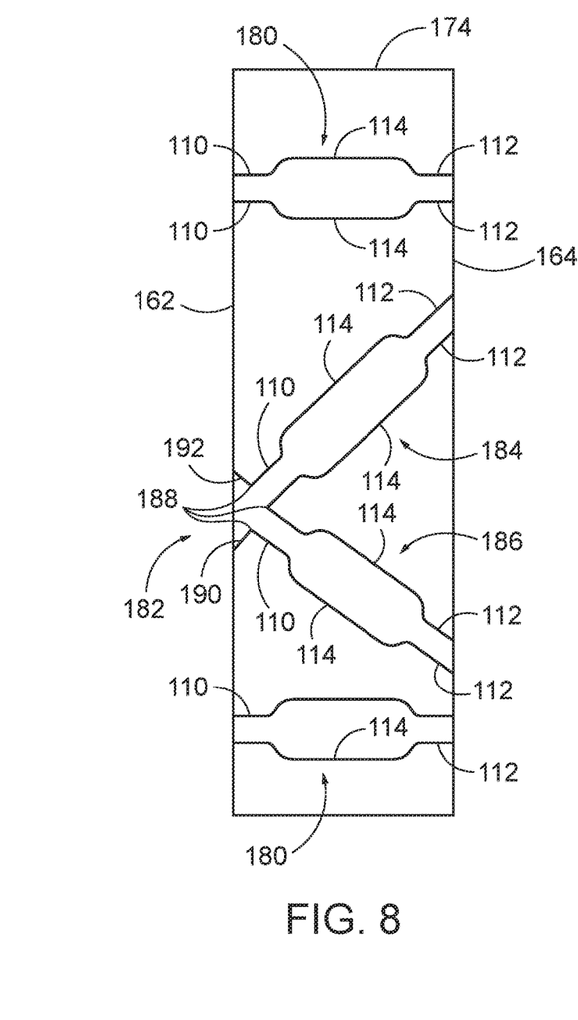
FIG. 8 depicts a cross-sectional side view of the cutting block of FIG. 5, taken along line 7-7 of FIG. 5.

Coronal cut guide slots (180) extend from proximal surface (162) to distal surface (164) and extend between lateral edges (170, 172). As best seen in FIG. 8, one coronal cut guide slot (180) is located near top edge (174) to guide a reciprocating bone saw (90) to perform anterior coronal cut (14); while another coronal guide slot (180) is located near bottom edge (176) to guide reciprocating bone saw (90) to perform posterior coronal cut (15).

A chamfer cut entry slot (182) is defined by proximal surface (162). Chamfer cut entry slot (182) diverges into a first chamfer cut guide slot (184) and a second chamfer cut guide slot (186), each extending into distal surface (164). Chamfer cut entry slot (182) is dimensioned to receive reciprocating bone saw (90) such that bone saw (90) may also further extend into either chamfer cut guide slot (184, 186). In particular, chamfer cut entry slot (182) includes a first lead in surface (190) configured to guide bone saw (90) into first chamfer cut guide slot (184); while chamfer cut entry slot (182) includes a second lead in surface (192) configured to guide bone saw (90) into second chamfer cut guide slot (186). Additionally, chamfer cut entry slot (182) is partially defined by three chamfered edges (188). First chamfer cut guide slot (184) is located to guide reciprocating bone saw (90) to perform anterior chamfer cut (18); while second chamfer cut guide slot (186) is located to guide reciprocating bone saw (90) to perform posterior chamfer cut (19).

Guide slots (180, 184, 186) are located between lateral edges (170, 172) so that cutting guide block (160) may remain in one individual piece. In other words, if guide slots (180, 184, 186) completely extended through lateral edge (170) and all the way through lateral edge (172), cutting guide block (160) would be divided into multiple pieces, which may reduce the precision of the four bone cuts (14, 15, 18, 19) relative to each other.

As mentioned above, traditionally, guide slots (80, 84, 86) have been narrow, with sidewalls that are flat and straight along the entire length of guide slots (80, 84, 86), to suitably guide bone saw (90) during bone sawing in accordance with the description above. However, since cutting guide block (160) of the present example is manufactured with an additive process, such as 3D printing, guide slots (180, 184, 186) may have altered dimensions configured to minimize contact with bone saw (90) while suitably guiding bone saw (90). Such altered dimensions of guide slots (180, 184, 186) may not have been possible using traditional molding and/or machining techniques.

Figure 9:
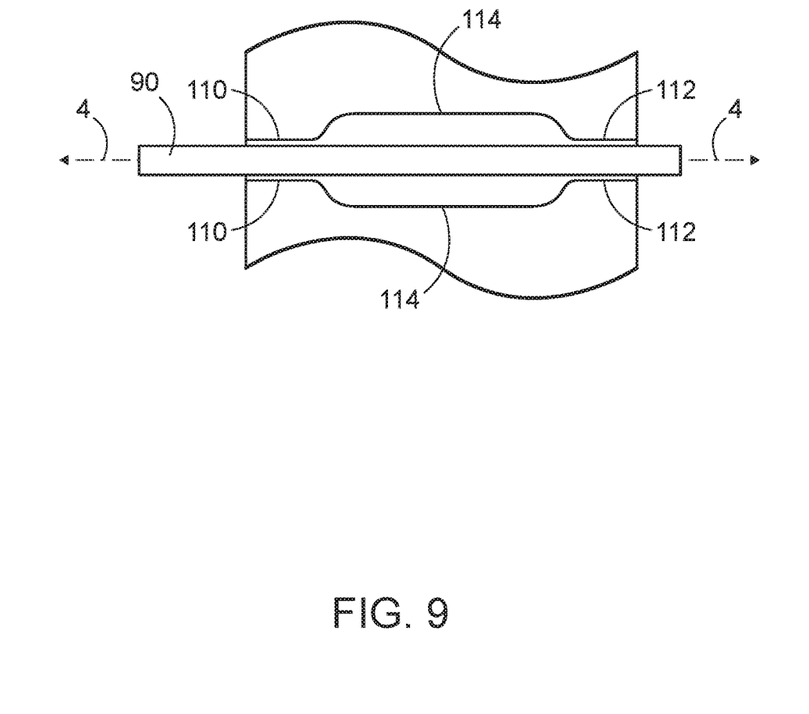
FIG. 9 depicts an enlarged cross-sectional side view of the cutting block of FIG. 5 with a bone saw inserted through a guide slot, taken along line 7-7 of FIG. 5.

In the current example, each guide slot (180, 184, 186) includes a pair of proximal interior surfaces (110), a pair of distal interior surfaces (112), and a pair of intermediate interior surfaces (114). Proximal interior surface (110) and distal interior surface (112) are both dimensioned to suitably guide bone saw (90) during exemplary use in accordance with the description above. Therefore, proximal interior surface (110) and distal interior surface (112) may contact bone saw (90) as bone saw (90) reciprocates in a sawing motion into and out of the page as viewed from above in FIG. 9. This reciprocation may generate heat through friction. However, intermediate interior surface (114) is recessed away from proximal interior surface (110) and distal interior surface (112). In other words, intermediate interior surface (114) is offset a distance away from insertion and retraction paths (4, 6, 8, 9) as compared to proximal interior surface (110) and distal interior surface (112). Therefore, as best seen in FIG. 9, as bone saw (90) reciprocates back and forth into and out of the page as viewed from above, bone saw (90) does not contact intermediate interior surface (114), such that less thermal energy builds as compared to guide slots (80, 84, 86) of cutting guide block (60) described above. It should be understood that proximal interior surface (110) and distal interior surface (112) still sufficiently contact bone saw (90) such that bone saw (90) is suitably aligned with insertion and retraction paths (4, 6, 8, 9). Chamfered edges (188) may also reduce friction with bone saw (90) when inserted through chamfer cut entry slot (182).

Figure 10:
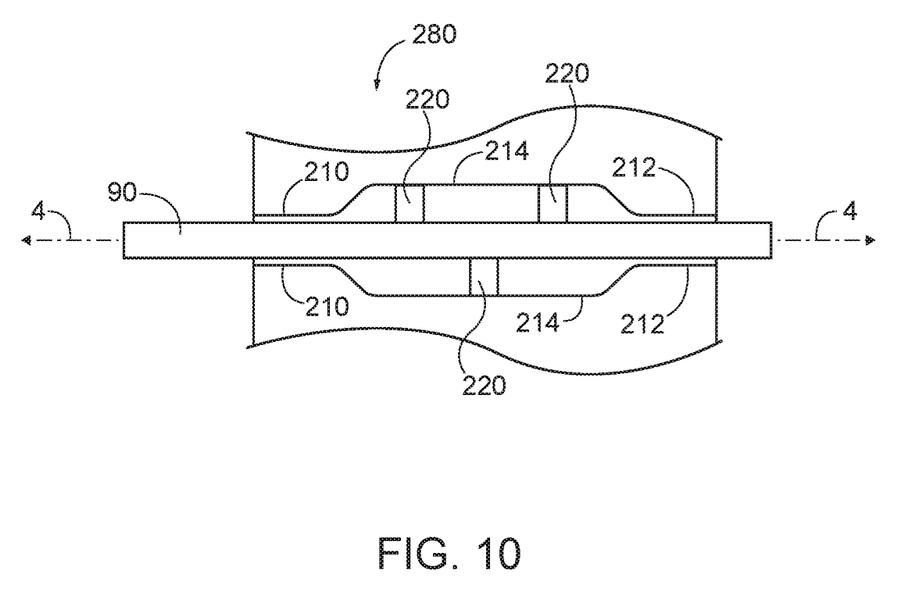
FIG. 10 depicts an enlarged cross-sectional side view of an alternative cutting block that may be used to resurface a femur in preparation of having a knee prosthesis attached, with a bone saw inserted through a guide slot.

In the current example, intermediate interior surface (114) is offset away from insertion and retraction paths (4, 6, 8, 9) as to not contact bone saw (90), while proximal interior surface (110) and distal interior surface (112) do contact and guide bone saw (90). However, this pattern is merely optional. FIG. 10 shows an alternative guide slot (280) that may be used instead of guides slots (180, 184, 186) described above. Guide slot has a proximal interior surface (210), a distal interior surface (212) and an intermediate interior surface (214); which are substantially similar to proximal interior surface (110), distal interior surface (112), and intermediate interior surface (114) described above. However, intermediate interior surface also comprises a plurality of ribs (220) that are also configured to contact bone saw (90) in order to keep bone saw (90) aligned with insertion and retraction paths (4, 6, 8, 9). Ribs (220) could allow proximal interior surface (210) and distal interior surface (212) to be shorter than previous proximal interior surface (110) and distal interior surface (112). Ribs (220) could be rectangular as shown, trapezoidal with a thicker base, or any other suitable geometry as would be apparent to one having ordinary skill in the art in view of the teachings herein. Ribs (220) could terminate at a point instead of being flat. Ribs (220) may run the entire length of a guide slot, or ribs (220) may be discretely placed at various locations along intermediate interior surface (214).

Any suitable pattern of surfaces offset away from insertion and retraction paths (4, 6, 8, 9) may be used as would be apparent to one having ordinary skill in the art in view of the teachings herein. For example, interior surfaces of slots (180, 184, 186) may be offset from insertion and retraction paths (4, 6, 8, 9) in a repetitive fashion in one or multiple directions, such as an undulating fashion, a zig-zag fashion, or a step fashion. It should still be understood that the portions of interior surfaces of slots (180, 184, 186) in contact with bone saw (90) may sufficiently align bone saw (90) with insertion and retraction paths (4, 6, 8, 9).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A bone saw cutting guide block, comprising: (a) a body, wherein the body comprises: (i) a proximal surface, (ii) a distal surface, (iii) a first lateral surface, and (iv) a second lateral surface; and (b) a bone saw guide assembly, wherein the bone saw guide assembly comprises a first guide slot defined by the body, wherein the first guide slot extends though the proximal surface and the distal surface along an insertion and retraction path, wherein the first guide slot extends between the first lateral surface and the second lateral surface, wherein the first guide slot is configured to accommodate lateral movement of a bone saw while guiding the bone saw along the insertion and retraction path, wherein the first guide slot comprises a first interior surface and a second interior surface, wherein the first interior surface is spaced a first distance transversely away from the insertion and retraction path, wherein the second interior surface is spaced a second distance transversely away from the insertion and retraction path, wherein the first distance is smaller than the second distance.

Example 2

The bone saw cutting guide block of Example 1, wherein the first interior surface is configured to contact the bone saw while guiding the bone saw along the insertion and retraction path, wherein the second interior surface is configured to not contact the bone saw while the first interior surface guides the bone saw along the insertion and retraction path.

Example 3

The bone saw cutting guide block of any one or more of Examples 1 through 2, wherein the body comprises a top edge, wherein the first guide slot extends distally at an oblique angle toward the top edge.

Example 4

The bone saw cutting guide block of Example 3, wherein the bone saw guide assembly further comprises a second guide slot defined by the body, wherein the second guide slot extends through the proximal surface and the distal surface, wherein the second guide slot extends between the first lateral surface and the second lateral surface.

Example 5

The bone saw cutting guide block of Example 4, wherein the body comprises a bottom edge, wherein the second guide slot extends distally at an oblique angle toward the bottom edge.

Example 6

The bone saw cutting guide block of Example 5, wherein the first guide slot and the second guide slot terminate proximally into an entry slot defined by the proximal surface.

Example 7

The bone saw cutting guide block of Example 6, wherein the body further comprises a first chamfered corned defining a portion of the entry slot, a portion of the first guide slot, and a portion of the second guide slot.

Example 8

The bone saw cutting guide block of Example 7, wherein the body further comprises a second chamfered corner defining a portion of the first guide slot.

Example 9

The bone saw cutting guide block of Example 8, wherein the body further comprises a third chamfered corner defining a portion of the second guide slot.

Example 10

The bone saw cutting guide block of any one or more of Examples 1 through 9, wherein the body defines a plurality of through holes extending through the proximal surface and the distal surface.

Example 11

The bone saw cutting guide block of any one or more of Examples 1 through 10, further comprising a plurality of ribs placed on the second interior surface.

Example 12

The bone saw cutting guide block of Example 11, wherein the first guide slot comprises a third interior surface, wherein the third interior surface is pace a first distance away from the insertion and retraction path.

Example 13

The bone saw cutting guide block of Example 12, wherein the third interior surface is distal relative to the second interior surface.

Example 14

The bone saw cutting guide block of Example 13, wherein the first interior surface is proximal relative to the second interior surface.

Example 15

The bone saw cutting guide block of any one or more of Examples 1 through 14, wherein the body is configured to selectively attach to a resurfaced femur.

Example 16

A bone saw cutting guide block, comprising: (a) a body, wherein the body comprises: (i) a proximal surface, (ii) a distal surface, (iii) a first lateral surface, and (iv) a second lateral surface; and (b) a bone saw guide assembly, wherein the bone saw guide assembly comprises a first guide slot defined by the body, wherein the first guide slot extends though the proximal surface and the distal surface along an insertion and retraction path, wherein the first guide slot is configured to accommodate lateral movement of a bone saw while guiding the bone saw along the insertion and retraction path, wherein the first guide slot comprises an offset surface configured to not contact the bone saw while the first interior surface guide the bone saw along the insertion and retraction path.

Example 17

The bone saw cutting guide block of Example 16, wherein the offset surface is located between the proximal surface and the distal surface.

Example 18

The bone saw cutting guide block of Example 17, wherein the first guide slot comprises a contact surface configured to contact the bone saw while guiding the bone saw along the insertion and retraction path.

Example 19

The bone saw cutting guide block of Example 18, wherein the contact surface is located distal and proximal relative to the offset surface.

Example 20

A bone saw cutting guide block, comprising: (a) a body, wherein the body comprises: (i) a proximal surface, (ii) a distal surface, and (iii) a chamfered corner, wherein the chamfered corner is located between the proximal surface and the distal surface, wherein the chamfered corner and the proximal surface define a laterally extending entry slot; and (b) a bone saw guide assembly, wherein the bone saw guide assembly comprises a first guide slot and a second guide slot, wherein the first guide slot extends from the laterally extending entry slot through the distal surface, and wherein the second guide slot extends from the laterally extending entry slot through the distal surface.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A bone saw cutting guide block, comprising:
   (a) a body, wherein the body comprises:
      (i) a proximal surface,
      (ii) a distal surface,
      (iii) a first lateral surface, and
      (iv) a second lateral surface; and
   (b) a bone saw guide assembly, wherein the bone saw guide assembly comprises a first guide slot defined by the body, wherein the first guide slot extends though the proximal surface and the distal surface along an insertion and retraction path, wherein the first guide slot extends between the first lateral surface and the second lateral surface, wherein the first guide slot is configured to accommodate lateral movement of a bone saw while guiding the bone saw along the insertion and retraction path, wherein the first guide slot comprises:
      (i) a first interior surface,
      (ii) a second interior surface,
      (iii) a third interior surface opposing the first interior surface, wherein the first interior surface and the third interior surface define a first gap,
      (iv) a fourth interior surface opposing the second interior surface, wherein the second interior surface and the fourth interior surface define a second gap that is larger than the first gap such that the second interior surface and the fourth interior surface are spaced a further distance away from the insertion and retraction path compared to the first interior surface and the third interior surface, respectively, wherein the first gap and the second gap are centrally aligned with the insertion and retraction path;
      (v) a first rib extending from the second interior surface toward the insertion and retraction path, and
      (vi) a second rib extending from the fourth interior surface toward the insertion and retraction path such that the first interior surface, the third interior surface, the first rib, and the second rib are configured to cooperatively retain the bone saw in alignment with the insertion and retraction path while accommodating lateral movement of the bone saw.

2. The bone saw cutting guide block of claim 1, wherein the second interior surface is configured to not contact the bone saw while the first interior surface guides the bone saw along the insertion and retraction path.

3. The bone saw cutting guide block of claim 1, wherein the body comprises a top edge, wherein the first guide slot extends distally at an oblique angle toward the top edge.

4. The bone saw cutting guide block of claim 3, wherein the bone saw guide assembly further comprises a second guide slot defined by the body, wherein the second guide slot extends through the proximal surface and the distal surface, wherein the second guide slot extends between the first lateral surface and the second lateral surface.

5. The bone saw cutting guide block of claim 4, wherein the body comprises a bottom edge, wherein the second guide slot extends distally at an oblique angle toward the bottom edge.

6. The bone saw cutting guide block of claim 5, wherein the first guide slot and the second guide slot terminate proximally into an entry slot defined by the proximal surface.

7. The bone saw cutting guide block of claim 6, wherein the body further comprises a first chamfered corned defining a portion of the entry slot, a portion of the first guide slot, and a portion of the second guide slot.

8. The bone saw cutting guide block of claim 7, wherein the body further comprises a second chamfered corner defining a portion of the first guide slot.

9. The bone saw cutting guide block of claim 8, wherein the body further comprises a third chamfered corner defining a portion of the second guide slot.

10. The bone saw cutting guide block of claim 1, wherein the body defines a plurality of through holes extending through the proximal surface and the distal surface.

11. The bone saw cutting guide block of claim 1, further comprising a plurality of ribs placed on the second interior surface.

12. The bone saw cutting guide block of claim 1, wherein the third interior surface is distal relative to the second interior surface.

13. The bone saw cutting guide block of claim 12, wherein the first interior surface is proximal relative to the second interior surface.

14. The bone saw cutting guide block of claim 1, wherein the body is configured to selectively attach to a resurfaced femur.

15. A bone saw cutting guide block, comprising:
 (a) a body, wherein the body comprises:
  (i) a proximal surface,
  (ii) a distal surface,
  (iii) a first lateral surface, and
  (iv) a second lateral surface; and
 (b) a bone saw guide assembly, wherein the bone saw guide assembly comprises a first guide slot defined by the body, wherein the first guide slot extends though the proximal surface and the distal surface along an insertion and retraction path, wherein the first guide slot is configured to accommodate lateral movement of a bone saw while guiding the bone saw along the insertion and retraction path, wherein the first guide slot comprises:
  (i) a first contact surface,
  (ii) a second opposing contact surface defining a first gap with the first contact surface,
  (iii) a first offset surface adjacent to the first contact surface,
  (iv) a second offset surface adjacent to the second opposing contact surface and defining a second gap with the first offset surface, wherein the second gap is larger than the first gap, wherein the first offset surface and the second offset surface are configured to not contact the bone saw while the first interior surface and the second opposing interior surface guide the bone saw along the insertion and retraction path,
  (v) a first rib extending from the first offset surface, and
  (vi) a second rib extending from the second offset surface, wherein the first rib, the second rib, the first interior surface, and the second opposing interior surface are configured to contact the bone saw while accommodating lateral movement of the bone saw and guiding the bone saw along the insertion and retraction path.

16. The bone saw cutting guide block of claim 15, wherein the first offset surface is located between the proximal surface and the distal surface.

17. The bone saw cutting guide block of claim 15, wherein the first rib and the second rib are offset along an axis defined by the proximal surface and the distal surface.

18. The bone saw cutting guide block of claim 17, wherein the first contact surface is located distal and proximal relative to the offset surface.

19. A bone saw cutting guide block, comprising:
 (a) a body, wherein the body comprises:
  (i) a proximal surface,
  (ii) a distal surface, and
  (iii) a chamfered corner, wherein the chamfered corner is located between the proximal surface and the distal surface, wherein the chamfered corner and the proximal surface define a laterally extending entry slot; and
 (b) a bone saw guide assembly, wherein the bone saw guide assembly comprises a first guide slot and a second guide slot, wherein the first guide slot extends from the laterally extending entry slot through the distal surface, and wherein the second guide slot extends from the laterally extending entry slot through the distal surface, wherein the first guide slot comprises a narrow entry portion defining a first gap and a widened central portion defining a second gap that is larger than the first gap, wherein the narrow entry portion is defined by a first contact surface and a second contact surface facing each other, wherein the widened central portion is defined by a first offset surface and a second offset surface, wherein the first offset surface and the second offset surface face each other, wherein the bone saw guide assembly further comprises a first rib extending from the first offset surface and a second rib extending from the second offset surface, wherein the first contact surface, the second contact surface, the first rib, and the second rib are configured to contact a bone saw while accommodating lateral movement of the bone saw and guiding the bone saw along an insertion and retraction path defined by the first guide slot, wherein the insertion and retraction path, the first gap, and the second gap are centrally aligned.

* * * * *